United States Patent
Chang et al.

(10) Patent No.: US 7,146,855 B1
(45) Date of Patent: Dec. 12, 2006

(54) CHECKING AND MEASURING SYSTEM FOR HUMAN BODY

(75) Inventors: Chin-Feng Chang, Taichung (TW); Seng-Chi Chen, Longtan Township, Taoyuan County (TW); Ming-Cheng Lin, Taiping (TW)

(73) Assignee: Fukuta Electric & Machinery Co., Ltd., Taichung Hsien (TW)

( * ) Notice: Subject to any disclaimer, the term of this patent is extended or adjusted under 35 U.S.C. 154(b) by 0 days.

(21) Appl. No.: 11/476,121

(22) Filed: Jun. 28, 2006

(51) Int. Cl.
*A61B 5/22* (2006.01)
(52) U.S. Cl. .................................. 73/379.01
(58) Field of Classification Search ............ 73/379.02, 73/379.01, 379.03
See application file for complete search history.

(56) References Cited

U.S. PATENT DOCUMENTS 4,982,613 A * 1/1991 Becker .................. 73/862.625
5,156,053 A * 10/1992 Shiraishi et al. ............... 73/849
6,149,550 A * 11/2000 Shteingold ...................... 482/8
6,904,801 B1 * 6/2005 Bridges et al. .......... 73/379.01
7,021,155 B1 * 4/2006 Imamura ...................... 73/797

* cited by examiner

*Primary Examiner*—Jewel Thompson
(74) *Attorney, Agent, or Firm*—Rosenberg, Klein & Lee (57) ABSTRACT

A checking and measuring system includes a checking and measuring mechanism, and a strength measuring element; the checking and measuring mechanism includes a rail, a moving rod positioned within the rail, a rotating power source connected to the moving rod, a sliding member movably connected to the moving rod and sliding along the rail, a first testing rod fitted on the sliding member, and a second testing rod fixed next to one end of the rail; the strength measuring element is fitted to the second testing rod; when a person holds both the testing rods with one hand, and holds a container containing a heavy metal pollutant with the other hand, with the index finger touching a piece of metal having the same element, strength of his/her hands will be measured, and the amount of the heavy metal in this person's body will be obtained based on results of measurement.

9 Claims, 7 Drawing Sheets

CHECKING AND MEASURING SYSTEM FOR HUMAN BODY

BACKGROUND OF THE INVENTION

1. Field of the Invention

The present invention relates to a checking and measuring system for human body, more particularly one, which can be used to find out how much heavy metal a person has in his/her body as well as for measuring the strength of the hands of patients suffering stroke and those suffering from brain diseases for accessing the performance of hand muscle rehabilitating treatment.

2. Brief Description of the Prior Art

Many kinds of heavy metals exist on the Earth, e.g. lead, cadmium, mercury, zinc, copper, chromium, and iron. They cannot be degraded or destroyed. To a small extent they enter our bodies via food, drinking water and air. As trace elements, some heavy metals are essential to maintain the metabolism of the human body. However, at higher concentrations they can lead to poisoning. Heavy metal poisoning could result, for instance, from drinking-water contamination or intake via the food chain. Heavy metals are dangerous because they tend to bioaccumulate. Bioaccumulation means an increase in the concentration of a chemical in a biological organism over time. Compounds accumulate in living things any time they are taken up and stored faster than they are broken down or excreted.

The followings outline the sources of common heavy metals, Lead, Cadmium, Mercury, and Zinc and the harms done by them:

1. Lead; Lead exposure can occur through drinking water, food, air, soil, gasoline, and dust from old paint containing lead; exposure to lead can result in a wide range of biological effects depending on the level and duration of exposure; high levels of exposure may result in toxic biochemical effects in humans which in turn cause effects on the kidneys, joints and reproductive system, and acute or chronic damage to the nervous system.

2. Cadmium; in humans, long-term exposure is associated with renal disfunction; high exposure can lead to obstructive lung disease and has been linked to lung cancer; Cadmium is produced as an inevitable by-product of zinc (or occasionally lead) refining; the most significant use of cadmium is in nickel/cadmium batteries.

3. Mercury; inorganic mercury poisoning causes damage to the nervous system, and the kidneys; the major source of mercury pollutants is discarded batteries.

4. Zinc; pesticide contains Zinc, and intake of too much pesticide will result in Zinc poisoning, which will do harm to livers.

Therefore, it is a main object of the present invention to provide a checking and measuring system for human body, which can be used to find out the amount of heavy metals a person has in his/her body as well as for measuring the strength of the hands of patients suffering stroke and those suffering from brain diseases for accessing the performance of hand muscle rehabilitating treatment.

SUMMARY OF THE INVENTION

The checking and measuring system of the present invention includes a checking and measuring mechanism, a strength detecting and measuring element, and a monitor. The checking and measuring mechanism includes a linear rail, a moving rod positioned within the linear rail, a rotating power source connected to the threaded moving rod, a sliding member movably connected to the threaded moving rod and sliding along the linear rail, a first testing rod fitted on the sliding member, and a second testing rod fixed next to one end of the linear rail and facing the first testing rod. The strength detecting and measuring element is fitted to the second testing rod while the monitor is connected to the strength detecting and measuring element. When a person holds both the testing rods with one hand, and holds a container containing a kind of heavy metal pollutant with the other hand, the index finger touching a piece of metal having the same element as the heavy metal pollutant, strength of his/her hands will be measured, and the amount of the heavy metal in this person's body will be obtained based on the maximum and the average value of the hands' strength. The checking and measuring system is also used to measure the strength of the hands of patients suffering stroke and those suffering from brain diseases for accessing the performance of hand muscle rehabilitating treatment.

BRIEF DESCRIPTION OF THE DRAWINGS

The present invention will be better understood by referring to the accompanying drawings, wherein.

DETAILED DESCRIPTION OF THE PREFERRED EMBODIMENTS

Referring to FIGS. 1 to 4, a preferred embodiment of a checking and measuring system for human body includes:

a checking and measuring mechanism 1, the checking and measuring mechanism 1 includes a linear rail 11, a moving rod 12 positioned within the linear rail 11, a flexible shaft coupling 13, a rotating power source 14, a sliding member 15, a blocking plate 151, a switch 16, testing rods 17 and 18, and a supporting member 19; the moving rod 12 can be a threaded rod 12, and the rotating power source 14 can be a motor; the flexible shaft coupling 13 is connected to one end of the moving rod 12 at a first end thereof for maintaining stability of motion of the moving rod 12; the flexible shaft coupling 13 is connected to the rotating power source 14 at the other end; the sliding member 15 is connected to the moving rod 12 in a movable manner, and can slide along the linear rail 11 while the blocking plate 151 is fitted on a lateral side of the sliding member 15 for use together with the switch 16; the switch 16 includes a leftmost stopping switch 161, a rightmost stopping switch 162, and a return-to-zero switch 163; the leftmost stopping switch 161 is positioned near to a left end of an outer side of the linear rail 11, the rightmost stopping switch 162 near to a right end of the outer side of the linear rail 11, and a return-to-zero switch 163 on an intermediate portion of the outer side of the linear rail 11; the testing rod 17 is fitted on the sliding member 15 while the testing rod 18 is secured on the supporting member 19 positioned on the left end of the linear rail 11, and faces the testing rod 17;

a power controlling device 2, the power controlling device 2 can be used together with a motion controlling card, and is connected to the rotating power source 14 for controlling the rotating power source 14 so that the rotating power source 14 rotates in one of forward and rearward directions;

a strength detecting and measuring element 3 fitted to the testing rod 18;

a junction box 7 connected to the strength detecting and measuring element 3;

a monitor 4 connected to the strength detecting and measuring element 3 for showing results of checking and measurement;

a computer 5 connected to the junction box 7 for storing results of checking and measurement; and a container 6 for containing heavy metal pollutants to be used in checking and measuring.

Figure 1:
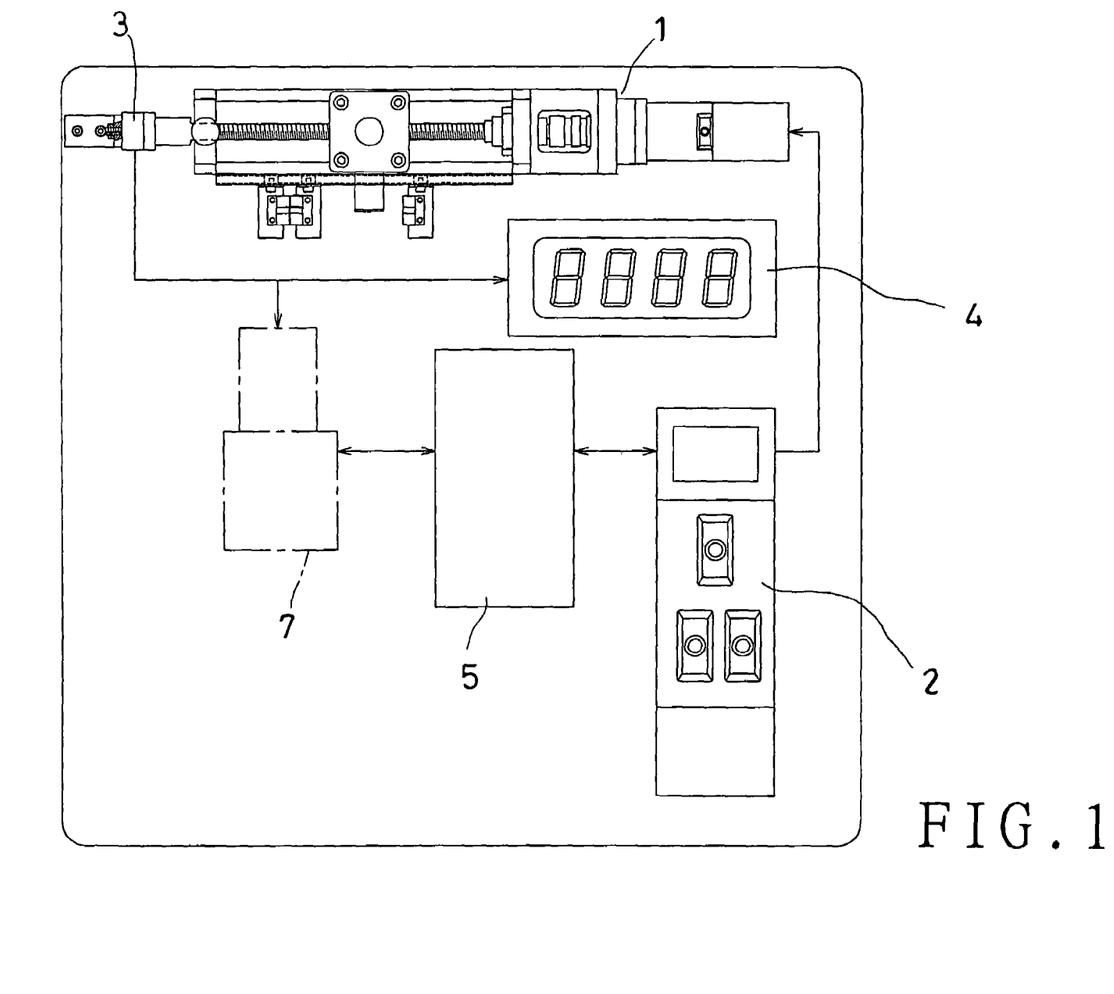
FIG. 1 is a vertical view of the present invention.
Figure 2:
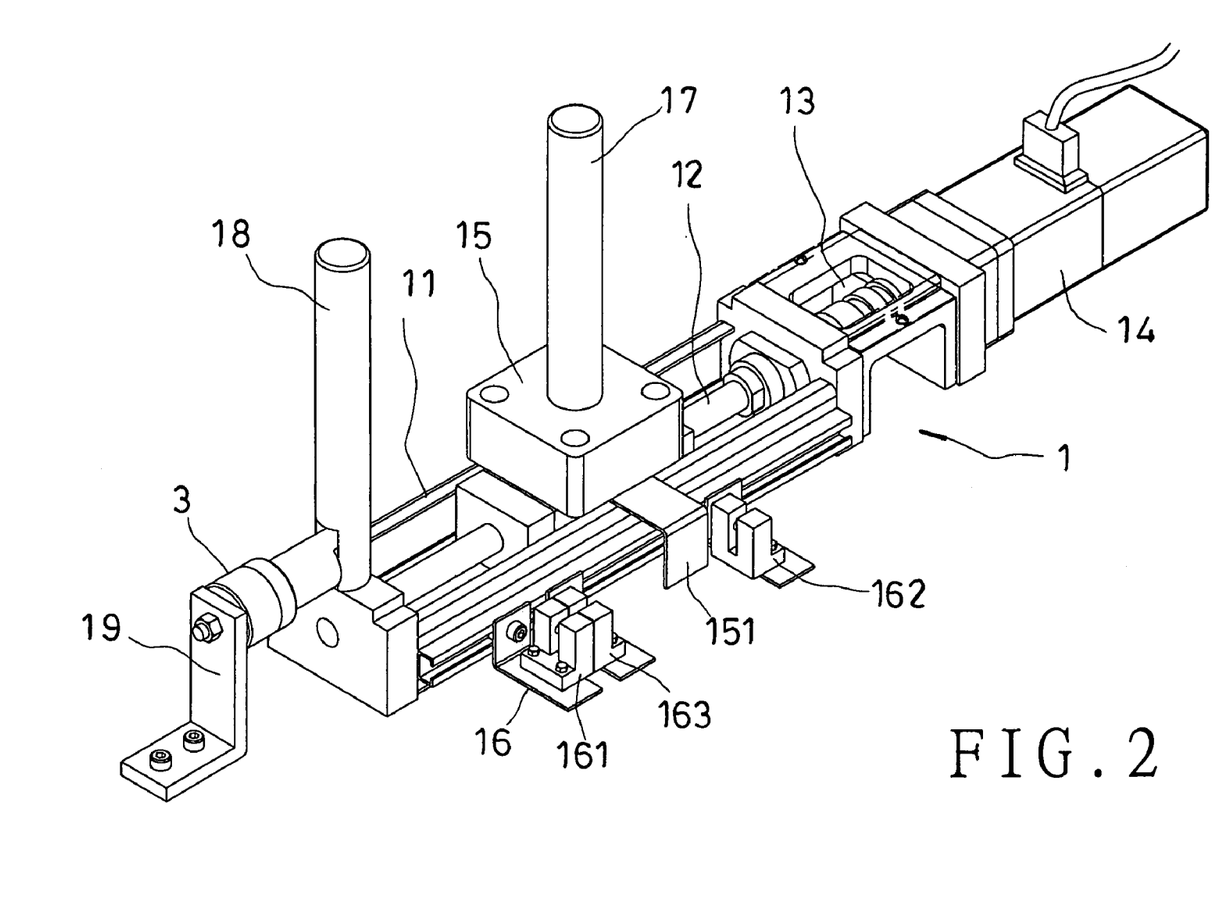
FIG. 2 is a perspective view of the present invention.
Figure 3:
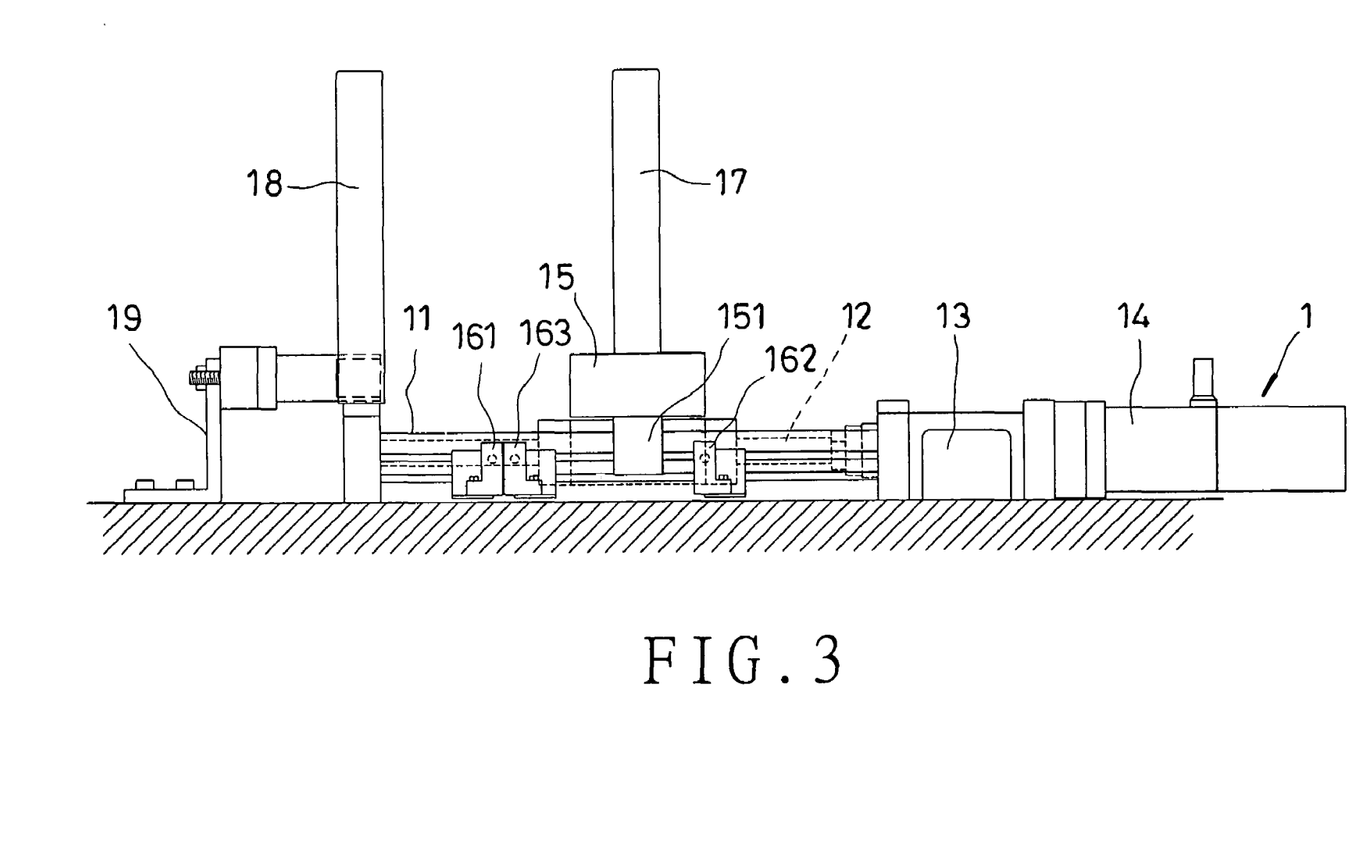
FIG. 3 is a front view of the present invention.
Figure 4:
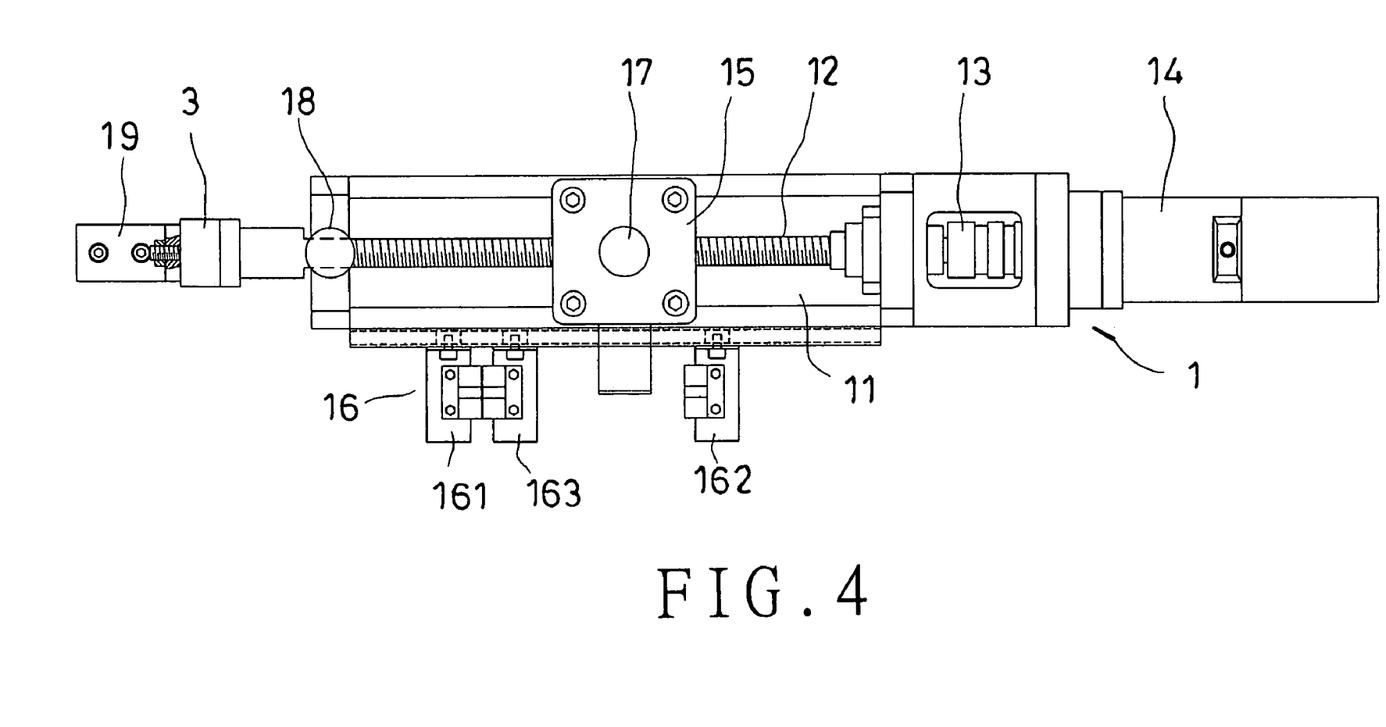
FIG. 4 is a partial vertical view of the present invention.
Figure 5:
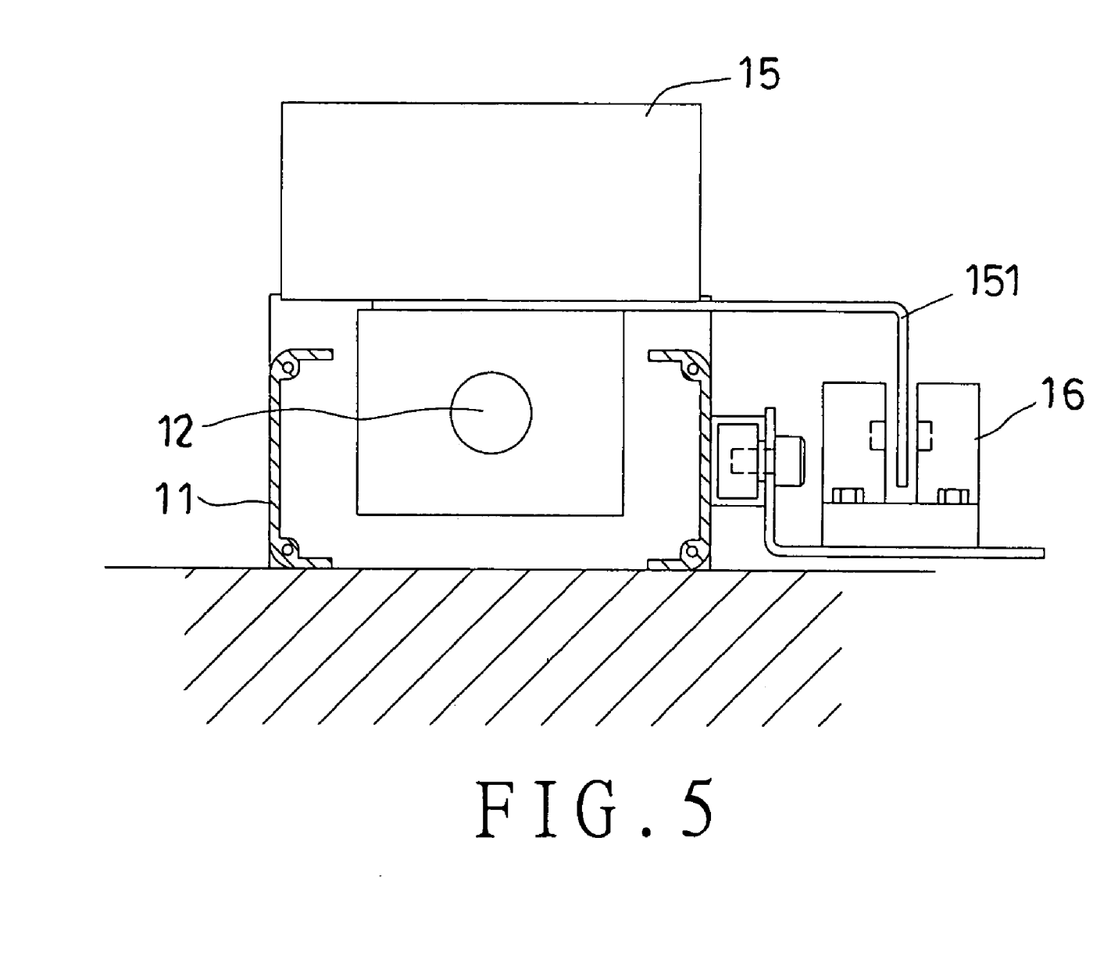
FIG. 5 is a side view of the present invention.
Figure 6:
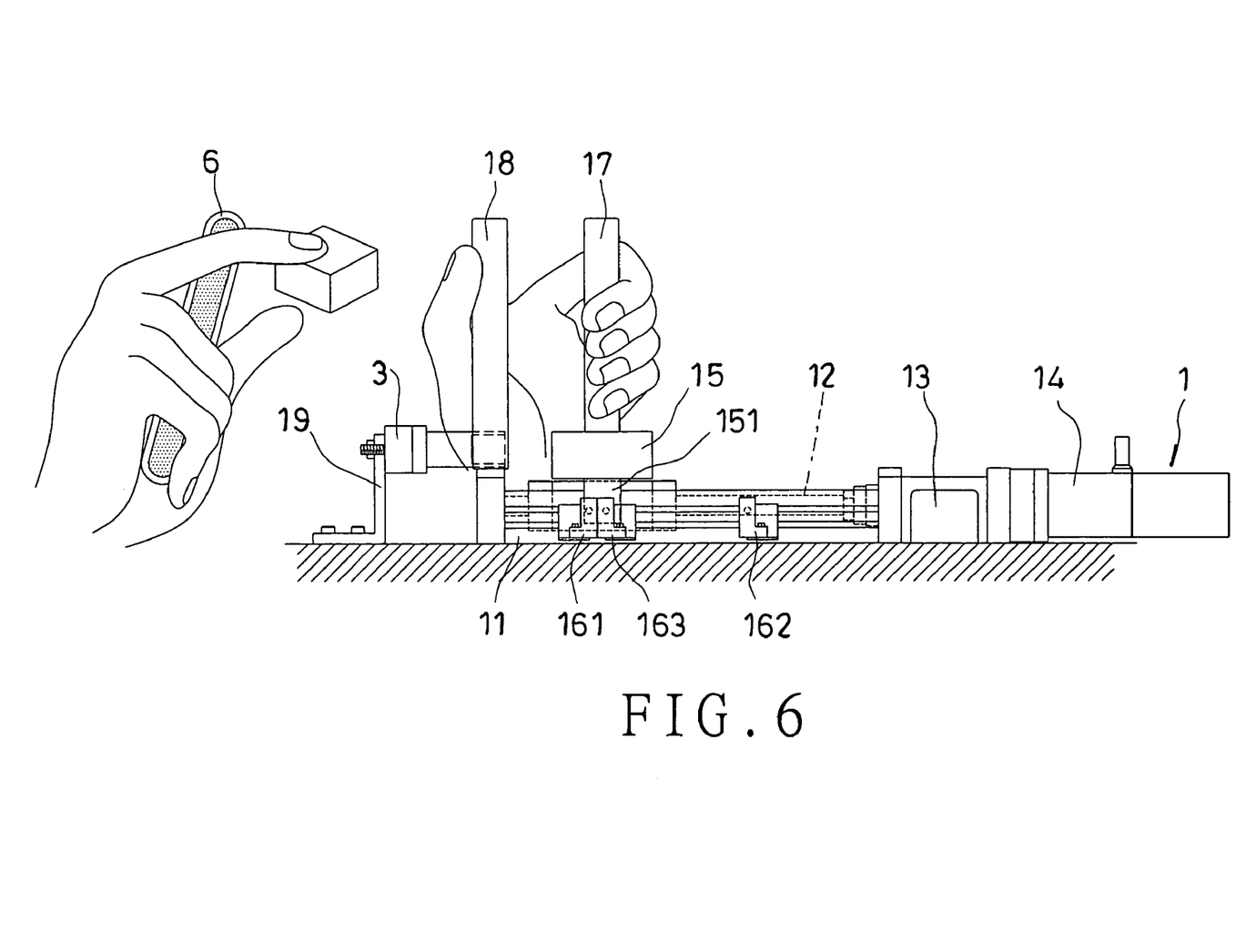
FIG. 6 is a view of the present invention, taken when it is being used (1)
Figure 7:
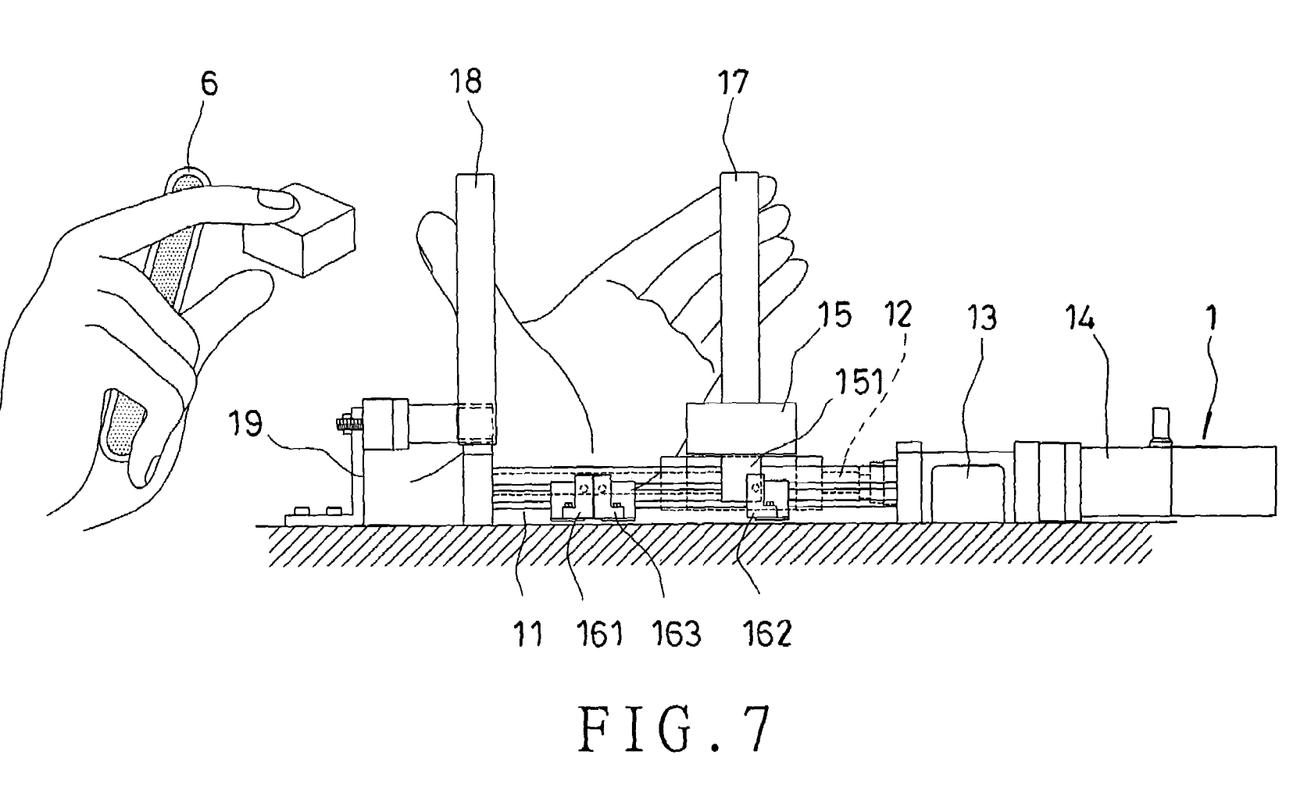
FIG. 7 is a view of the invention, taken when it is being used (2)

Referring to FIGS. 6 and 7, the power controlling device 2 is activated to make the rotating power source 14 start rotating to move the sliding member 15 to the return-to-zero switch 163; thus, the monitor 4 shows a zero value. Next, a person to be examined holds a-container, in which a heavy metal pollutant is held, with a first hand, and touches a piece of metal having the same element as the heavy metal pollutant with the index finger of the first hand, and he/she holds the testing rods 17 and 18 with the other (second) hand with the thumb being pressed against the testing rod 17, and the four fingers being pressed against the testing rod 18. Because the heavy metal pollutant and the piece of metal have the same element, they have the same wavelength and frequency, and will cause resonance of the person's brain wave, and in turn the person's hands become strengthless; the greater amount of heavy metal this person has in his/her body, the more strengthless his/her hands will become. Therefore, when the rotating power source 14 moves the sliding member 15 and testing rod 17 rightwards away from the testing rod 18, the holding force on the testing rods 17 and 18 will reduce owing to strength loss of the person's hands. The strength detecting and measuring element 3 will measure the strength of the person's hands immediately after the sliding member 15 and the testing rod 17 stop at a certain position. Next, the maximum value and the average value of the strength of the person's hands are shown on the monitor 4, and transferred to and stored in the computer 5 so that a database of patients is built, based on which values the amount of the heavy metal in this person's body will be obtained. The above process is preferably repeated two or three times to obtain more accurate values. If the amount of a heavy metal in the person's body is found to exceed the normal range, he/she should receive treatment as soon as possible.

In addition, the checking and measuring system of the present invention can be used to access the performance of hand muscle rehabilitating treatment given to patients suffering stroke and those suffering from brain diseases by means of measuring the strength of the patients' hands. In carrying out a check with the present system, a patient should hold both the testing rods 17 and 18 with his/her hands; thus, the hands' strength can be found out through the strength detecting and measuring element 3 after the rotating power source 14 is actuated to move the testing rod 17 away from the testing rod 18 until the testing rod 17 stops at a predetermined position.

From the above description, it can be seen that the present invention has the following advantages:

1. The strength of a person's hands can be measured by means of the checking and measuring system of the present invention, and the amount of the heavy metal in this person's body will be obtained based on the maximum and the average value of the hands' strength. Therefore, if the amount of a heavy metal in a person's body exceeds the normal range, early detection is possible, allowing him/her to receive treatment without delay.

2. The checking and measuring system of the present invention will be a good apparatus in preventive medicine; the amount of a heavy metal in a person's body can be obtained by means of the checking and measuring system. In other words, he/she will know if the amount of a heavy metal in the body doesn't exceed the normal range, but is relatively large, allowing him/her to prevent this situation from getting worse.

3. The flexible shaft coupling is interposed between the moving rod and the rotating power source therefore the moving rod is prevented from shaking to reduce the accuracy of measurement.

4. The checking and measuring system of the present invention can be used to access the performance of muscle rehabilitating treatment given to patients suffering stroke and those suffering from brain diseases.

What is claimed is:

1. A checking and measuring system for human body, comprising
    (a) a checking and measuring mechanism, the checking and measuring mechanism including:
    a linear rail,
    a moving rod positioned within the linear rail,
    a rotating power source connected to one end of the moving rod,
    a sliding member connected to the moving rod in a movable manner, the sliding member being capable of sliding along the linear rail;
    a first testing rod fitted on the sliding member, and
    a second testing rod, the second testing rod being fixed next to one end of the linear rail and facing the first testing rod;
    (b) a strength detecting and measuring element fitted to the second testing rod, and
    (c) a monitor connected to the strength detecting and measuring element.

2. The checking and measuring system for human body as recited in claim 1 further having a flexible shaft coupling interposed between and connected to the moving rod and the rotating power source.

3. The checking and measuring system for human body as recited in claim 1 further having a power controlling device connected to the rotating power source for controlling rotational direction of the rotating power source.

4. The checking and measuring system for human body as recited in claim 3, wherein the power controlling device is used together with a motion controlling card.

5. The checking and measuring system for human body as recited in claim 1 further having a blocking plate, and a switch; the blocking plate being fitted on a lateral side of the sliding member for use together with the switch; the switch including a leftmost stopping switch positioned near to a left end of an outer side of the linear rail, a rightmost stopping switch near to a right end of the outer side of the linear rail, and a return-to-zero switch on an intermediate portion of the outer side of the linear rail.

6. The checking and measuring system for human body as recited in claim 1, wherein the moving rod is a threaded rod.

7. The checking and measuring system for human body as recited in claim 1, wherein the rotating power source is a motor.

8. The checking and measuring system for human body as recited in claim 1, wherein the strength detecting and measuring element is connected to a computer used for storing results of checking and measurement to build a database of patients.

9. The checking and measuring system for human body as recited in claim 1 further having a container for containing heavy metal pollutants to be used in checking and measuring; in checking and measuring, a person holds the container, in which a heavy metal pollutant is held, with a first hand, and touches a piece of metal having a same element as the heavy metal pollutant with the index finger of the first hand, and he/she holds both the testing rods with other hand.

* * * * *